United States Patent
Tsuang et al.

(10) Patent No.: US 8,784,493 B2
(45) Date of Patent: Jul. 22, 2014

(54) INTERVERTEBRAL CAGE AND IMPLANTING APPARATUS AND OPERATING METHOD THEREOF

(75) Inventors: Yang-Hwei Tsuang, Taipei (TW); Huang-Chien Liang, Hsinchu (TW); Chang-Jung Chiang, Taipei (TW); Chia-Hsien Chen, New Taipei (TW); Fon-Yih Tsuang, Taipei (TW); Yung-Fang Tsai, Taichung (TW)

(73) Assignee: Wiltrom Co., Ltd., Hsinchu County (TW)

( * ) Notice: Subject to any disclaimer, the term of this patent is extended or adjusted under 35 U.S.C. 154(b) by 404 days.

(21) Appl. No.: 13/117,618

(22) Filed: May 27, 2011

(65) Prior Publication Data
US 2012/0209383 A1    Aug. 16, 2012

(30) Foreign Application Priority Data

Feb. 14, 2011    (TW) .............................. 100104834 A

(51) Int. Cl.
*A61F 2/44*        (2006.01)
*A61B 17/70*       (2006.01)

(52) U.S. Cl.
USPC .......................... 623/17.16; 606/99; 606/279

(58) Field of Classification Search
USPC .............. 606/99, 249, 279; 623/17.11, 17.16
See application file for complete search history.

(56) References Cited

U.S. PATENT DOCUMENTS

| | | | |
|---|---|---|---|
| 7,500,991 B2 | 3/2009 | Bartish, Jr. et al. | |
| 7,976,549 B2 * | 7/2011 | Dye et al. | 606/99 |
| 8,147,554 B2 * | 4/2012 | Hansell et al. | 623/17.16 |
| 8,506,629 B2 * | 8/2013 | Weiland | 623/17.11 |
| 2004/0127990 A1 | 7/2004 | Bartish et al. | |
| 2005/0096745 A1 | 5/2005 | Andre et al. | |
| 2005/0119747 A1 | 6/2005 | Fabris Monterumici et al. | |
| 2007/0067035 A1 | 3/2007 | Falahee | |
| 2007/0093901 A1 | 4/2007 | Grotz et al. | |
| 2007/0225726 A1 | 9/2007 | Dye et al. | |
| 2007/0260314 A1 | 11/2007 | Biyani | |
| 2007/0270951 A1 | 11/2007 | Davis et al. | |
| 2008/0147194 A1 | 6/2008 | Grotz et al. | |
| 2009/0054991 A1 | 2/2009 | Biyani et al. | |
| 2009/0222092 A1 | 9/2009 | Davis et al. | |
| 2010/0094422 A1 | 4/2010 | Hansell et al. | |
| 2010/0204798 A1 * | 8/2010 | Gerbec et al. | 623/17.16 |

FOREIGN PATENT DOCUMENTS

TW           201036589           10/2010

* cited by examiner

*Primary Examiner* — Nicholas Woodall
*Assistant Examiner* — Larry E. Waggle, Jr.
(74) *Attorney, Agent, or Firm* — Rabin & Berdo, P.C.

(57) ABSTRACT

An intervertebral cage, an implanting apparatus and an operating method thereof are provided. The intervertebral cage for being implanted between two adjacent vertebral bodies includes a body and a connecting portion. The body has a lateral convex surface, an inclined surface, a lateral concave surface and a connecting surface connected sequentially. The connecting portion includes a main portion and a protrusion. The main portion connected to the connecting surface has a through hole. The protrusion is protruded from the main portion into the through hole to form first and second inner arc surfaces. The maximum width of the intervertebral cage is a distance between first and second lines. The first and second lines are substantially parallel to a tangent line of the lateral convex surface and the first line, respectively. The distance between the inclined surface and the first line decreases gradually along a direction away from the connecting portion.

16 Claims, 12 Drawing Sheets

INTERVERTEBRAL CAGE AND IMPLANTING APPARATUS AND OPERATING METHOD THEREOF

This application claims the benefit of Taiwan application Serial No. 100104834, filed Feb. 14, 2011, the subject matter of which is incorporated herein by reference.

BACKGROUND

1. Technical Field

The disclosure relates in general to an intervertebral cage, an implanting apparatus and an operating method thereof, and more particularly to an intervertebral cage used for being implanted into a location between adjacent vertebral bodies, an implanting apparatus used for implanting the intervertebral cage and an operating method thereof.

2. Description of the Related Art

The main functions of the spine are for supporting and protecting important nerve tissues. The spine includes a number of vertebral bodies and intervertebral discs. Each intervertebral disc is located between two top-down vertebral bodies to relieve stress by absorbing the pressure generated from vertebral bodies. The intervertebral discs further serve as pivots for enabling the human body to rotate or bend, and are thus crucial to the human body. However, the intervertebral discs having been pressed by local stresses over a long period of time tend to degenerate or even become herniated so as to suppress the nerves. Thus, degenerated or herniated intervertebral discs would cause acute pain and such pain is hard to relieve.

One of the most commonly used therapies is to remove the intervertebral disc that suppresses the nerve or the spinal cord through a surgical operation. In general, the clinical surgeon would first perform excision on the intervertebral disc. Then, the patient's autologous bone is implanted into a hole formed following the excision of the intervertebral disc. Thus, two top-down vertebral bodies and the patient's implanted autologous bone can be fused to restore the stability of the spine. However, if the original spine is already unstable, too many (more than two) intervertebral discs are excised, or the amount of bone implantation is too large, then an intervertebral cage (also known as spinal interbody fusion cage) is implanted into a location between the vertebral bodies to assure the success of bone fusion and avoid the implanted autologous bone being broken or exfoliated due to overload.

Despite minimally invasive surgery has become popular in the field of clinical orthopedics, orthopedics surgical instruments such as intervertebral cages still need certain sizes and shapes to assure the appropriate stability, so that the created wound is at least 5 cm. Also, in terms of uniform distribution of stress, the shapes of ordinary intervertebral cages do not match with the shapes of the patient's vertebral bodies, so the stress received by the intervertebral cage is not uniformly distributed. Provided that the intervertebral cage whose shape is close to that of the vertebral body is available, such type of the intervertebral cage is normally too large. Thus, nerves or great vessels are hard to be bypassed, and injuries are very likely to be resulted. Thus, how to provide an intervertebral cage which is conformed to the requirements of the minimally invasive surgery and capable of resolving the above mentioned disadvantages has become an imminent task for the industries.

SUMMARY

The disclosure is directed to an intervertebral cage, an implanting apparatus and an operating method thereof. The coupling column and the sleeve of the implanting apparatus clamp the intervertebral cage at different positions for implanting the intervertebral cage. Besides, the corporation between the lateral convex surface and the inclined surface makes the implantation easier.

According to a first aspect of the present disclosure, an intervertebral cage for being implanted into a location between two adjacent vertebral bodies is provided. The intervertebral cage includes a body and at least one connecting portion. The body has a lateral convex surface, a lateral concave surface, an inclined surface and a connecting surface. The lateral convex surface, the inclined surface, the lateral concave surface and the connecting surface are connected sequentially. The connecting portion includes a main portion and a first protrusion. The main portion is connected to the connecting surface of the body, and has a through hole. The first protrusion is protruded from the main portion into the through hole in a direction towards the connecting surface so as to form a first inner arc surface and a second inner arc surface. The maximum width of the intervertebral cage is a distance between a first line and a second line. The first line is substantially parallel to a tangent line of the lateral convex surface. The second line is substantially parallel to the first line. The distance between the inclined surface and the first line decreases gradually along a direction away from the connecting portion.

According to a second aspect of the present disclosure, an implanting apparatus used for implanting an intervertebral cage into a location between two adjacent vertebral bodies is provided. The implanting apparatus includes a sleeve and an extension member. The extension member has a rod and a coupling column. The rod is screwed inside the sleeve. The coupling column is connected to one end of the rod, and exposed outside the sleeve. The axial direction of the coupling column is substantially perpendicular to that of the rod. When one end of the coupling column is disposed on an inner arc surface of a connecting portion of the intervertebral cage and the rod is rotated with respect to the sleeve, the distance between the coupling column and the sleeve is decreased so as to clamp the connecting portion of the intervertebral cage between the coupling column and the sleeve.

According to a third aspect of the present disclosure, an operating method is provided. The operating method includes the following steps. An implanting apparatus and an intervertebral cage are provided. Wherein, the implanting apparatus includes a sleeve and an extension member, the extension member has a rod and a coupling column; the rod is screwed inside the sleeve, the coupling column is connected to one end of the rod and exposed outside the sleeve, the axial direction of the coupling column is substantially perpendicular to that of the rod; the intervertebral cage includes a connecting portion, the connecting portion includes a main portion and a protrusion; the main portion has at least one through hole, and the protrusion is protruded from the main portion into the through hole so as to form a first inner arc surface and a second inner arc surface. Then, the implanting apparatus is moved, so that the coupling column of the implanting apparatus is located at one side of the connecting portion of the intervertebral cage. After that, the implanting apparatus is rotated, so that one end of the coupling column is received in the through hole of the connecting portion and adjacent to the first inner arc surface. Then, the rod is rotated with respect to the sleeve along a rotation direction, so that a distance between the sleeve and the coupling column is decreased to clamp the connecting portion between the coupling column and the sleeve and the end of the coupling column presses against the first inner arc surface.

The above and other aspects of the disclosure will become better understood with regard to the following detailed description of the non-limiting embodiment(s). The following description is made with reference to the accompanying drawings.

DETAILED DESCRIPTION

Figure 1A:
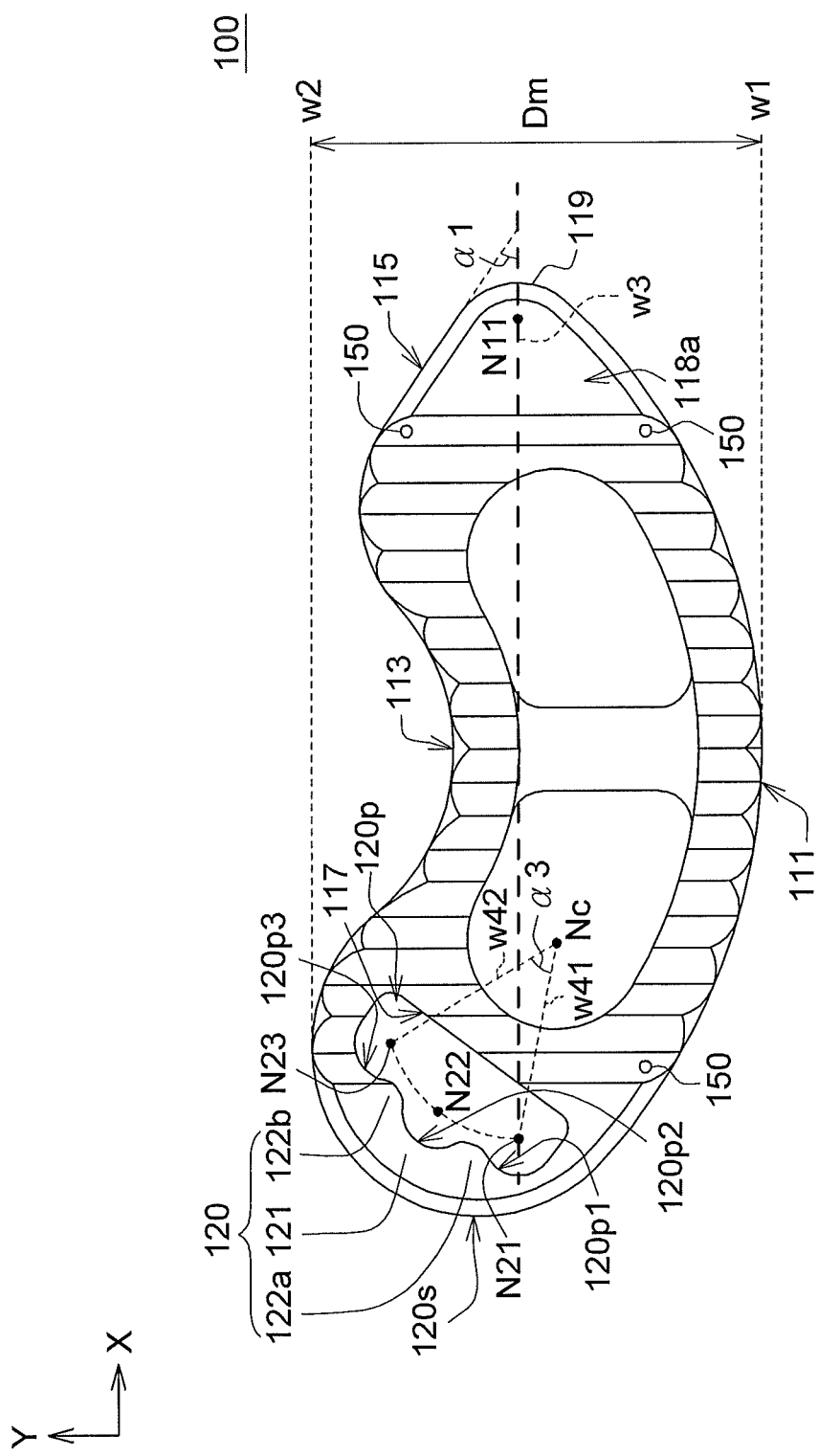
FIGS. 1A~1D are diagrams respectively showing the intervertebral cage viewed from different view angles according to an embodiment of the disclosure.
Figure 1B:
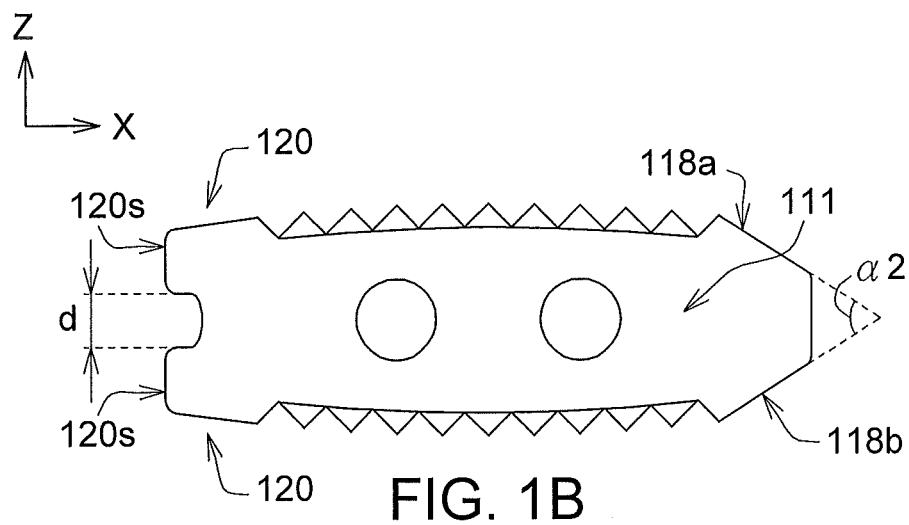
Figure 1C:
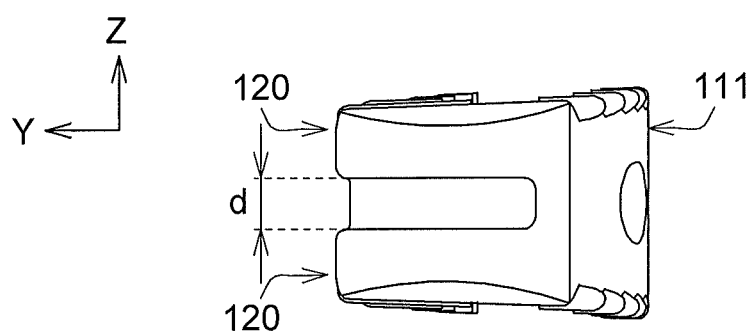
Figure 1D:
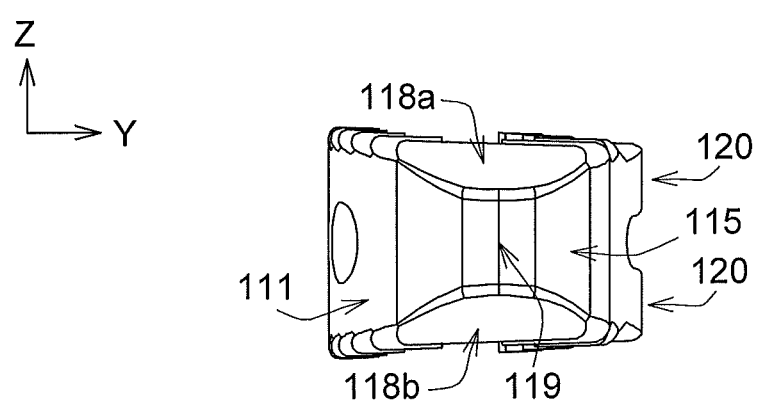
Figure 1E:
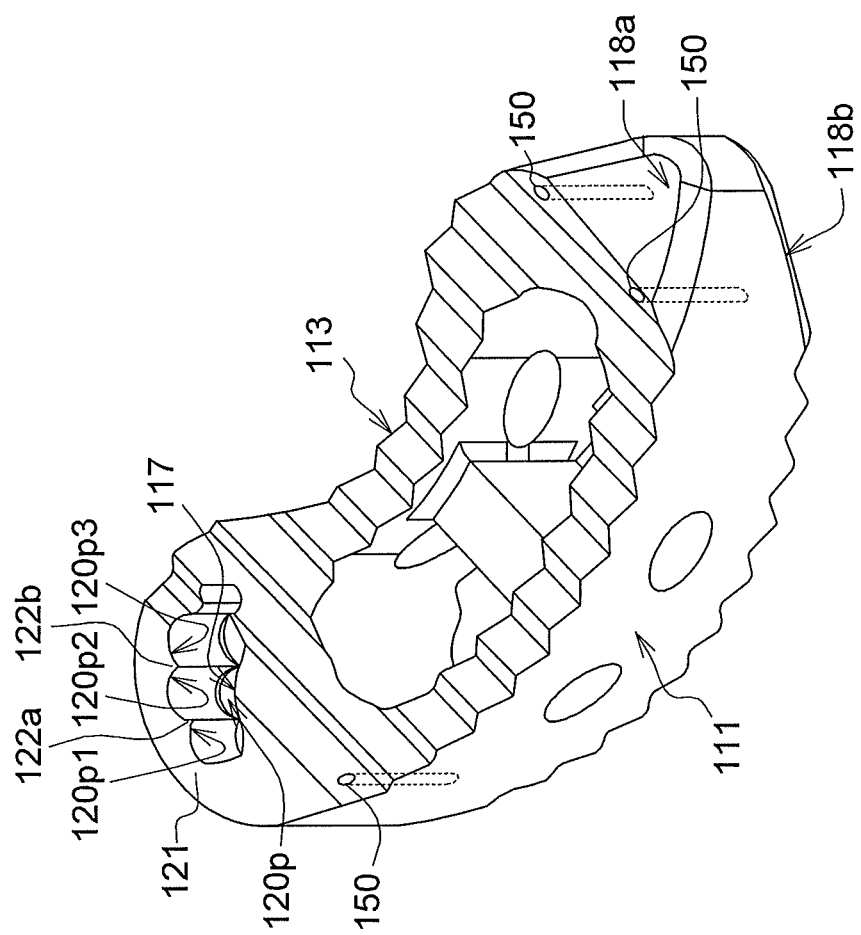
FIGS. 1E and 1F respectively show 3-D diagrams of the intervertebral cage of FIGS. 1A~1D viewed from different view angles.
Figure 1F:
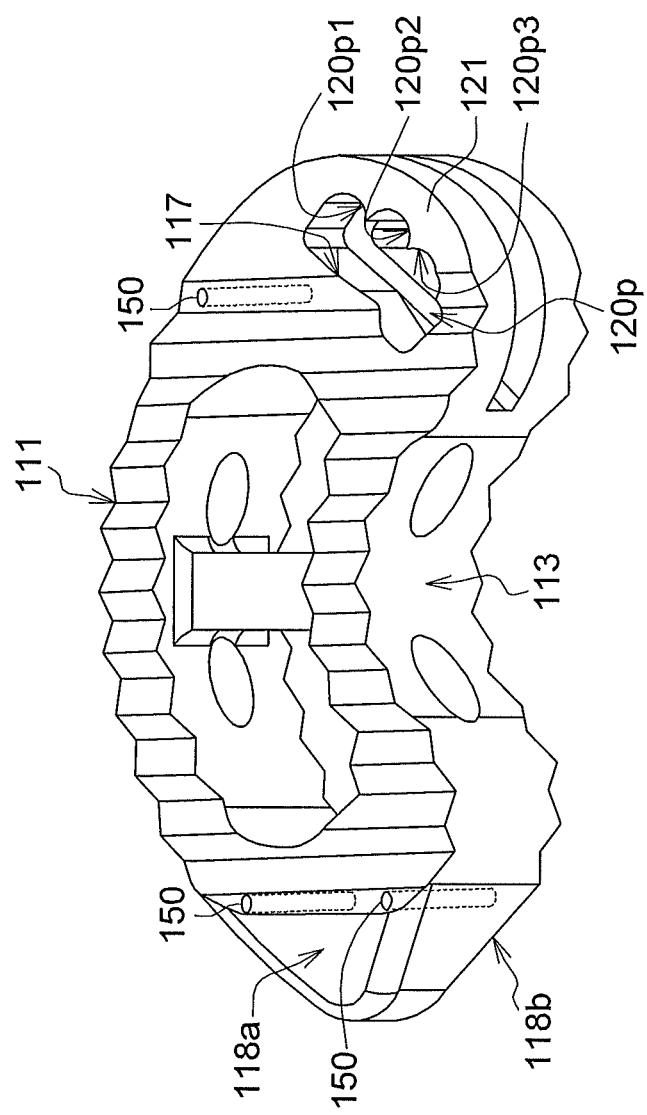
Figure 1G:
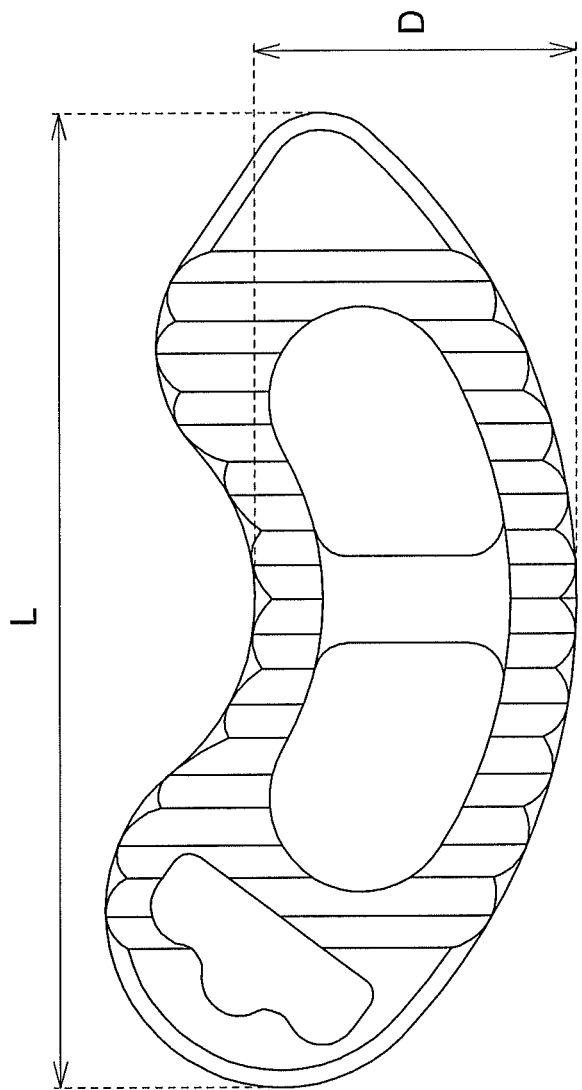
FIG. 1G shows the intervertebral cage of FIG. 1A designated with length and width.
Figure 2A:
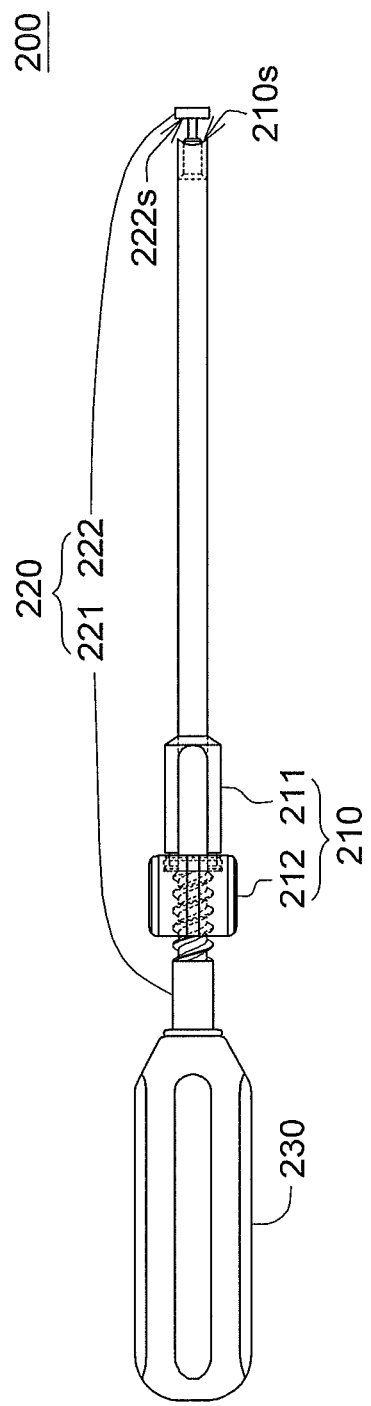
FIGS. 2A and 2B respectively show an assembly diagram and an explosion diagram of the implanting apparatus according to an embodiment of the disclosure.
Figure 2B:
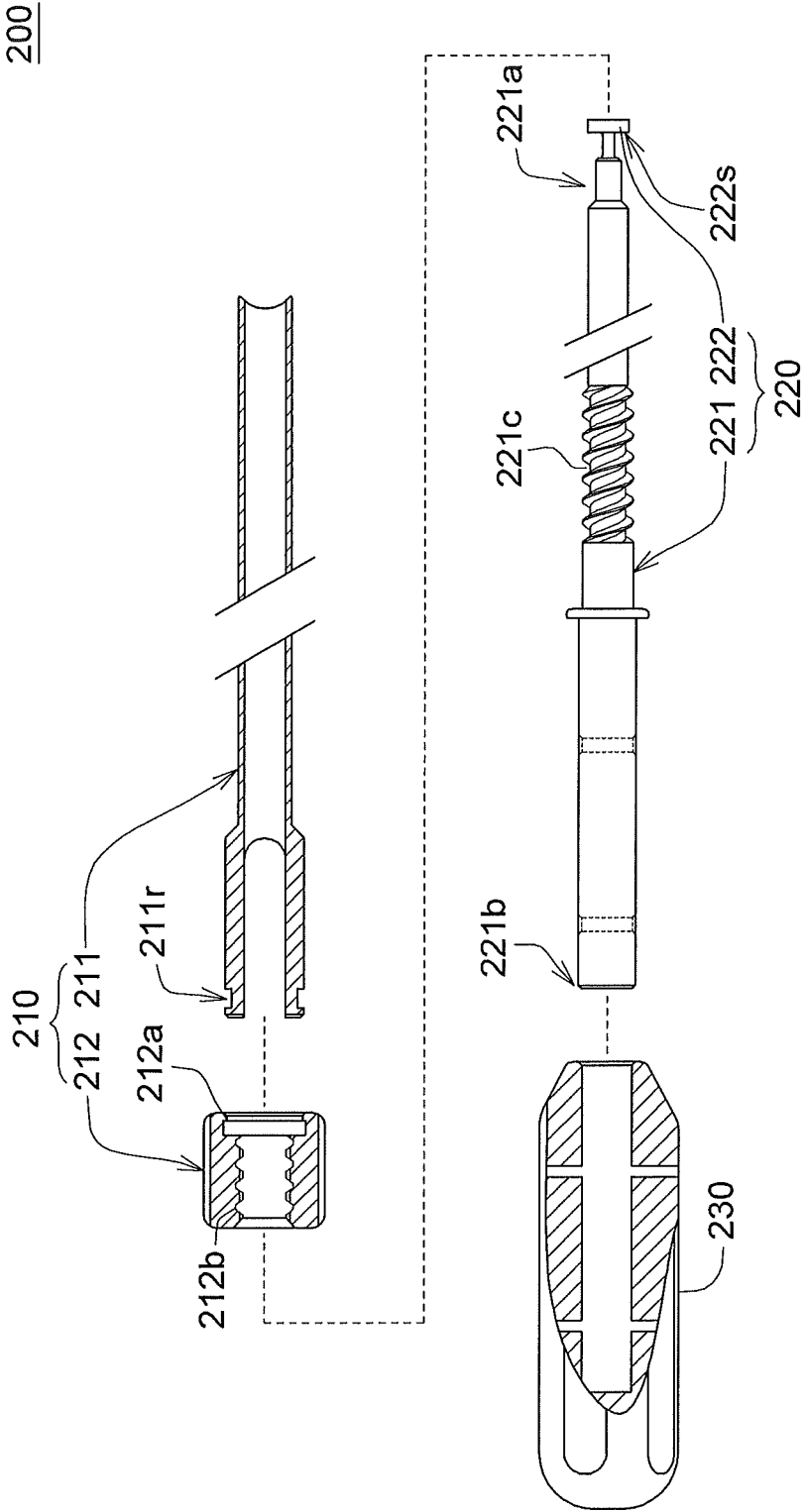

Firstly, the structures of an intervertebral cage 100 (as indicated in FIGS. 1A~1G) and an implanting apparatus 200 (as indicated in FIGS. 2A and 2B) of the present embodiment of the disclosure are disclosed. Next, processes of clamping the intervertebral cage 100 by the implanting apparatus 200 are elaborated with accompanying drawings FIGS. 3A~3C. Lastly, processes of implanting the intervertebral cage 100 into a location between two adjacent vertebral bodies by the implanting apparatus 200 are elaborated with accompanying drawings FIGS. 4A~4F Referring to FIGS. 1A~1G, diagrams respectively showing the intervertebral cage 100 viewed from different view angles according to an embodiment of the disclosure are shown in FIGS. 1A~1D, 3-D diagrams of the intervertebral cage 100 of FIGS. 1A~1D viewed from different view angles are respectively shown in FIGS. 1E and 1F, and the intervertebral cage 100 of FIG. 1A designated with length L and width D is shown in FIG. 1G. The intervertebral cage 100 is used for being implanted into a location between two adjacent vertebral bodies. The intervertebral cage 100 includes a body (disclosed below) and two connecting portions 120, for example.

The body has a lateral convex surface 111, a lateral concave surface 113, an inclined surface 115 and a connecting surface 117. The lateral convex surface 111, the inclined surface 115, the lateral concave surface 113 and the connecting surface 117 are connected sequentially.

In the present embodiment of the disclosure, the two connecting portions 120 have similar structures, and are spaced by a distance d. Each connecting portion 120 includes a main portion 121, a first protrusion 122a and a second the protrusion 122b. The main portion 121 is connected to the connecting surface 117 of the body, and has a through hole 120p. The first protrusion 122a is protruded from the main portion 121 into the through hole 120p in a direction towards the connecting surface 117, and the second the protrusion 122b is protruded from the main portion 121 into the through hole 120p in a direction towards the connecting surface 117 so as to form a first inner arc surface 120p1, a second inner arc surface 120p2 and a third inner arc surface 120p3. The second inner arc surface 120p2 is located between the first inner arc surface 120p1 and the third inner arc surface 120p3.

In the present embodiment of the disclosure, the implanting end of the body facilitates the implantation of the intervertebral cage 100, and is elaborated below.

The disposition of the inclined surface 115 is elaborated first. In the present embodiment of the disclosure, the maximum width Dm of the intervertebral cage 100 is a distance between the first line segment w1 and the second line segment w2. The first line segment w1 is substantially parallel to a tangent line of the lateral convex surface 111 along the X-axis direction, and the second line segment w2 is substantially parallel to the first line segment w1. In the present embodiment of the disclosure, the distance between the inclined surface 115 and the first line segment w1 decreases gradually along a direction away from the connecting portion 120 (that is, the X-axis direction). The body further has a fillet 119 which is located between the inclined surface 115 and the lateral convex surface 111.

In terms of the top surface 118a and the bottom surface 118b (as indicated in FIG. 1B) of the body, the bottom surface 118b is opposite to the top surface 118a, and the top surface 118a and the bottom surface 118b are both located between the lateral convex surface 111 and the lateral concave surface 113.

An angle $\alpha 1$ contained between the inclined surface 115 and a line segment w3 connecting the circle center N11 of the fillet 119 to the circle center N21 of the first inner arc surface 120p1 ranges 0~89 degrees, 0~60 degrees or 0~45 degrees. An angle $\alpha 2$ contained between the top surface 118a and the bottom surface 118b at the junction between the inclined surface 115 and the lateral convex surface 111 ranges 1~179 degrees, 1~135 degrees or 1~90 degrees.

When the angle $\alpha 1$ is a large angle (such as 60~89 degrees) and the angle $\alpha 2$ is also a large angle (such as 135~179 degrees), the inclined surface 115, the lateral convex surface 111, the fillet 119, the top surface 118a and the bottom surface 118b of the body together form an obtuse implanting end to avoid the intervertebral cage 100 being deviated during implantation so as to damage surrounding nerve tissues. Thus, the intervertebral cage 100 can be safely implanted.

In the present embodiment of the disclosure, when the angle $\alpha 1$ is a small angle (0~45 degrees) and the angle $\alpha 2$ is a small angle (1~90 degrees), the inclined surface 115, the lateral convex surface 111, the fillet 119, the top surface 118a and the bottom surface 118b of the body together form an acute implanting end. In general, when a tiny wound is created for removing an intervertebral disc, the intervertebral disc cannot be completely removed and may have some remnants left. Thus, during the process of implanting an object into a location between two vertebral bodies, the remnants of the intervertebral disc will increase resistance to implantation. Since the implanting end of the intervertebral cage 100 of the present embodiment of the disclosure is an acute angle, the implanting end can easily peel off the annulus fibrosis of the intervertebral disc and effectively reduce the resistance caused by the remnants of the intervertebral disc. Therefore, the intervertebral cage 100 can be implanted into a location between two adjacent vertebral bodies in a manner that is convenient to applying force and performing surgery. In other words, the process of implanting the intervertebral cage 100 into a location between two adjacent vertebral bodies is made easier.

When the angle $\alpha 1$ is an angle ranges between the above-mentioned large angle and small angle but is closer to the large angle and when the angle $\alpha 2$ is an angle ranges between the abovementioned large angle and small angle but is closer to the large angle, the intervertebral cage 100 can be safely implanted. When the angle α1 is an angle ranges between the abovementioned large angle and small angle but is closer to the small angle and when the angle α2 is an angle ranges between the abovementioned large angle and small angle but is closer to the small angle, the intervertebral cage 100 can be implanted conveniently.

Let the circle center N21 of the first inner arc surface 120p1, the circle center N22 of the second inner arc surface 120p2 and the circle center N23 of the third inner arc surface 120p3 be three points on a circle. A first line segment w41 connects the circle center Nc of the circle to the circle center N21 of the first inner arc surface 120p1, and a second line segment w42 connects the circle center Nc of the circle to the circle center N23 of the third inner arc surface 120p3. An angle α3 contained between the first line segment w41 and the second line segment w42 ranges 0~179 degrees, 0~90 degrees or 45~75 degrees. In the present embodiment, the angle α3 ranges 45~75 degrees.

In the present embodiment of the disclosure, the intervertebral cage 100 further includes at least one positioning member 150 disposed inside the body as indicated in FIGS. 1A, 1E and 1F. The positioning member 150 can be made from a metal or a material that is not transmissible to X-ray. Thus, through the disposition of the positioning member 150, the surgeon can identifies the position of the intervertebral cage 100 with a surgical C-arm. The two connecting portions 120 and the body can be integrally formed in one piece. Furthermore, the intervertebral cage 100 can be made from an absorbable polymer material, a non-absorbable polymer material, a metal, a ceramic material, a bone material or a combination thereof. For example, the materials of the intervertebral cage 100 include a composite material formed by an absorbable polymer material and a ceramic material. The absorbable polymer material can be either poly(glycolide-co-lactide acid) (PLGA) or poly-l-lactic acid (PLLA). The non-absorbable polymer can be used is polyetheretherketone (PEEK). Examples of metal include titanium and stainless steel. The bone material may be obtained from human body or other animals.

As indicated in FIG. 1G, the width of the intervertebral cage 100 is designated by D, and the length of the intervertebral cage 100 is designated by L. The width D of the intervertebral cage 100 ranges 8~14 mm, and the length L of the intervertebral cage 100 ranges 26~30 mm. Anyone who is skilled in the technology of the disclosure will understand that the width D and the length L of the intervertebral cage 100 can be determined according to patients' needs.

Referring to FIGS. 2A and 2B, an assembly diagram and an explosion diagram of the implanting apparatus 200 according to an embodiment of the disclosure are respectively shown. The implanting apparatus 200 includes a sleeve 210, an extension member 220 and a handle 230.

The extension member 220 has a rod 221 and a coupling column 222. The rod 221 is screwed inside the sleeve 210. The coupling column 222 is connected to one end 221a of the rod 221 and exposed outside the sleeve 210, and the handle 230 is fixed at the other end 221b of the rod 221. The axial direction of the coupling column 222 is substantially perpendicular to that of the rod 221.

The implanting apparatus 200 of the present embodiment of the disclosure is further elaborated below. The rod 221 has outer screw threads 221c. The sleeve 210 includes a securing tube 211 and a locking member 212. The securing tube 211 and the locking member 212 both are hollowed structures. The outer surface of the securing tube 211 has a recess 211r, and the inner surface of the locking member 212 has a lump 212a and inner screw threads 212b. The securing tube 211 and the locking member 212 are detachably coupled by receiving the lump 212a in the recess 211r. The rod 221 is received in the securing tube 211 and the locking member 212 of the sleeve 210, and the coupling column 222 is exposed. The outer screw threads 221c of the rod 221 are screwed to the inner screw threads 212b of the locking member 212. Thus, when the rod 221 rotates with respect to the sleeve 210, the rod 221 moves along the sleeve 210, so that the distance between the sleeve 210 and the coupling column 222 connected to the end 221a of the rod 221 can be changed.

In the present embodiment of the disclosure, the sleeve 210 includes two parts (that is, the securing tube 211 and the locking member 212). However, anyone who is skilled in the technology of the disclosure will understand that the sleeve 210 can be integrally formed in one piece.

Figure 3A:
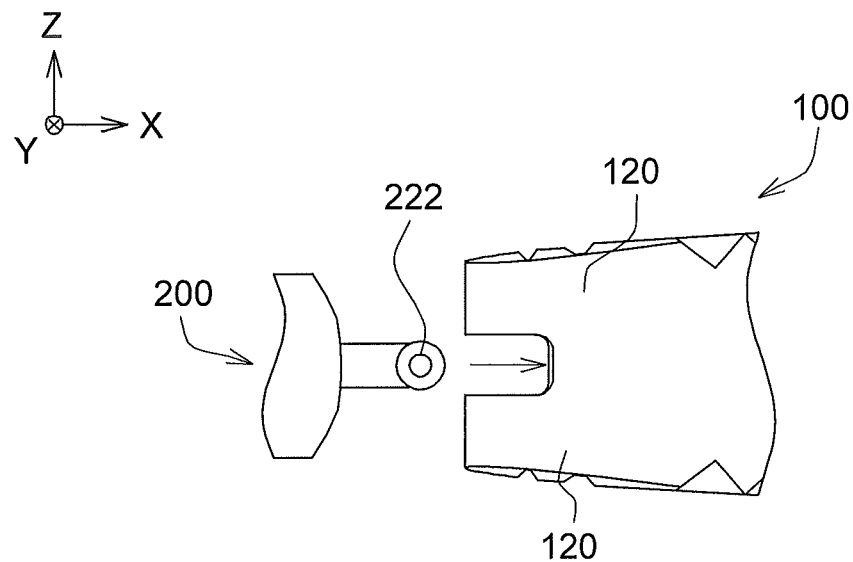
FIGS. 3A~3C are processes of clamping the intervertebral cage of FIGS. 1A~1G through the implanting apparatus of FIGS. 2A and 2B.
Figure 3B:
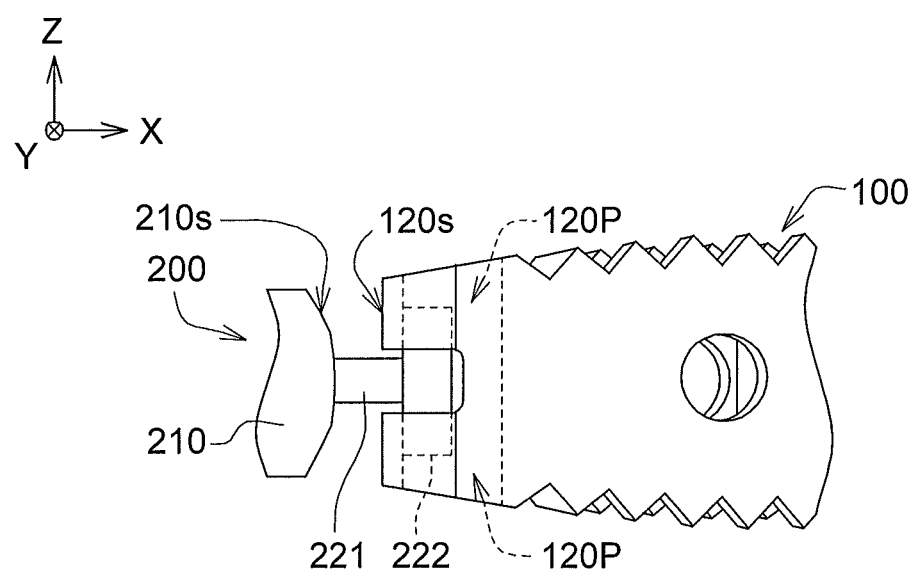
Figure 3C:
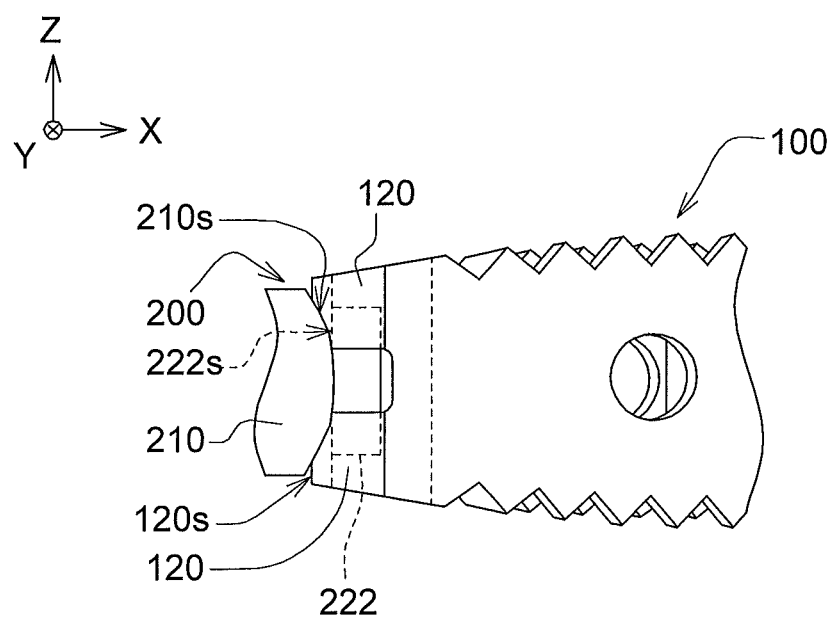

Please refer to FIGS. 2A, 2B, 3A~3C. FIGS. 3A~3C are processes of clamping the intervertebral cage 100 of FIG. 1A~1G through the implanting apparatus 200 of FIGS. 2A and 2B. The processes of clamping the intervertebral cage 100 through the implanting apparatus 200 are elaborated below with accompanying drawings FIGS. 3A~3C.

As indicated in FIG. 3A, the implanting apparatus 200 is moved along the X-axis direction, so that the coupling column 222 is located at one side of each connecting portion 120, that is, the coupling column 222 is inserted into a location between the two connecting portions 120. Meanwhile, the axial direction of the coupling column 222 is parallel to a Y-axis direction.

As indicated in FIG. 3B, after the coupling column 222 is inserted to the location between the two connecting portions 120, the implanting apparatus 200 is rotated around the X-axis, so that the axial direction of the coupling column 222 is parallel to a Z-axis direction. Thus, the two ends of the coupling column 222 are respectively disposed inside the two through holes 120p.

When the rod 221 is rotated with respect to the sleeve 210 along a rotation direction, the distance between the coupling column 222 and the sleeve 210 is decreased to clamp the connecting portions 120 of the intervertebral cage 100 therebetween as indicated in FIG. 3C. Meanwhile, the terminal end of the sleeve 210 contacts each connecting portion 120, and the two ends of the coupling column 222 respectively press against the two first inner arc surfaces 120p1, the two second inner arc surfaces 120p2 or the two third inner arc surfaces 120p3 (as indicated in FIG. 1A) according to which element the two ends of the coupling column 222 of FIG. 3B are adjacent to. That is, if the two ends of the coupling column 222 of FIG. 3B are adjacent to the two first inner arc surfaces 120p1 of the two connecting portions 120, then the two ends of the coupling column 222 will respectively press against the two first inner arc surfaces 120p1 as illustrated in FIG. 3C. If the two ends of the coupling column 222 of FIG. 3B are adjacent to the two second inner arc surfaces 120p2 of the two connecting portions 120, then the two ends of the coupling column 222 respectively press against the two second inner arc surfaces 120p2 as illustrated in FIG. 3C. If the two ends of the coupling column 222 of FIG. 3B are adjacent to the two third inner arc surfaces 120p3 of the two connecting portions 120, then the two ends of the coupling column 222 respectively press against the two third inner arc surfaces 120p3 as illustrated in FIG. 3C.

In the present embodiment of the disclosure, the rotation direction can be clockwise or counter-clockwise. In addition, for the coupling column 222 and the sleeve 210 to clamp the connecting portions 120 more firmly, the outline of the outer surface 210s of the terminal end of the sleeve 210 is substantially identical to that of the outer surface 120s of each connecting portion 120, and the outline of the outer surface 222s of the coupling column 222 is substantially identical to that of the two first inner arc surfaces 120p1, the two second inner arc surfaces 120p2 and the two third inner arc surfaces 120p3 as indicated in FIG. 1A.

To change the position at which the coupling column 222 and the sleeve 210 clamp the intervertebral cage 100, the rod 221 is rotated with respect to the sleeve 210 along a direction opposite to the rotation direction, so that the distance between the coupling column 222 and the sleeve 210 is increased to release the connecting portions 120. That is, if the rotation direction is clockwise and the distance between the coupling column 222 and the sleeve 210 is decreased by rotating the rod 221 clockwise with respect to the sleeve 210, then the distance between the coupling column 222 and the sleeve 210 is increased by rotating the rod 221 counter-clockwise with respect to the sleeve 210, and vice versa. Next, the implanting apparatus 200 is moved, so that the two ends of the coupling column 222 are adjacent to the targeted location such as the two second inner arc surfaces 120p2 (as indicated in FIG. 1A). However, such exemplification is not for limiting the disclosure. Then, the rod 221 is rotated with respect to the sleeve 210 along the rotation direction, so that the distance between the sleeve 210 and the coupling column 222 is decreased to clamp the connecting portions 120 therebetween. Thus, the two ends of the coupling column 222 press against the second inner arc surfaces 120p2.

To separate the intervertebral cage 100 from the implanting apparatus 200, the rod 221 is first rotated with respect to the sleeve 210 along the direction opposite to the rotation direction, so that the distance between the coupling column 222 and the sleeve 210 is increased to release the connecting portions 120. Then, the implanting apparatus 200 is rotated around the X axis, so that the axial direction of the coupling column 222 changes to being parallel to Y-axis direction from being parallel to the Z-axis direction, and the two ends of the coupling column 222 are departed from the through holes 120p of the connecting portion 120s. Thus, the implanting apparatus 200 can be removed.

The method and processes of implanting the intervertebral cage 100 by using the implanting apparatus 200 are elaborated below with accompanying drawings FIGS. 4A~4F. Referring to FIGS. 4A~4F, processes of implanting the intervertebral cage 100 of FIGS. 1A~1G by using the implanting apparatus 200 of FIGS. 2A and 2B are shown.

Figure 4A:
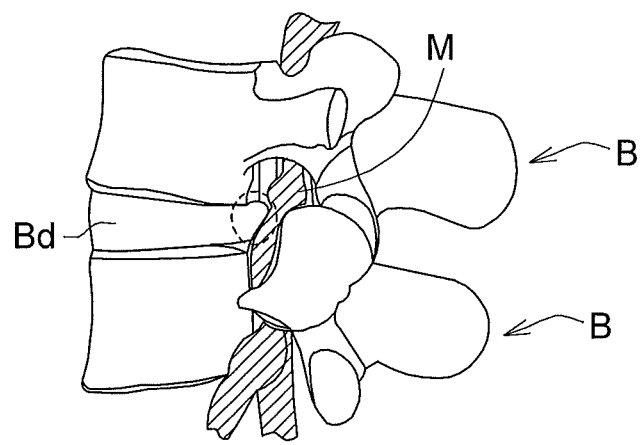
FIGS. 4A~4F are processes of implanting the intervertebral cage of FIGS. 1A~1G by using the implanting apparatus of FIGS. 2A and 2B.

As indicated in FIG. 4A, suppose a portion (circled by dotted lines) of an intervertebral disc Bd located between two adjacent vertebral bodies B of a patient degenerates or herniates to suppress a nerve M. To highlight the location of the nerve M, the nerve M is marked with slanted lines in FIG. 4A.

Figure 4B:
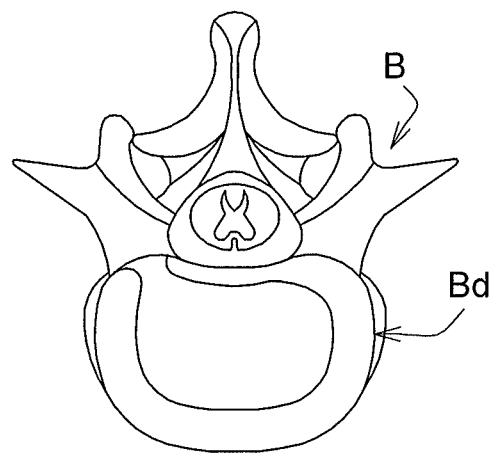

As indicated in FIG. 4B, the tissues (such as bone fragments or the intervertebral disc Bd) which suppress the nerve M or spinal cord in FIG. 4A are normally removed through a surgical operation, and after surgery, the spine is fixed with a spinal fixator and the intervertebral cage 100.

Figure 4C:
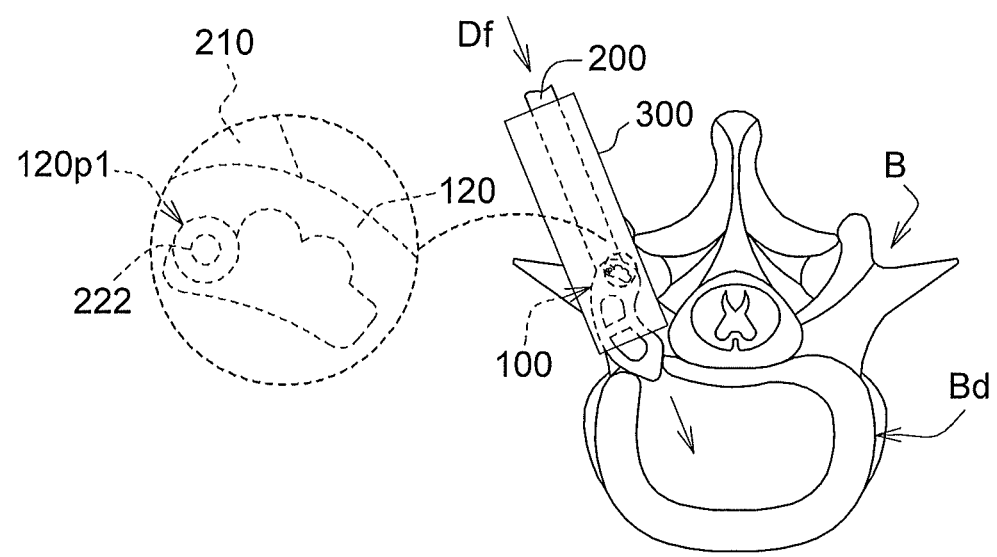

As indicated in FIG. 4C, a hollowed catheter 300 is disposed at one side of the vertebral body B adjacent to the intervertebral disc Bd, and the intervertebral cage 100 is implanted into a hole created after the excision of the intervertebral disc Bd by way of transforaminal lumbar interbody fusion (TLIF). The implanting apparatus 200 clamps the intervertebral cage 100 according to the processes illustrated in FIGS. 3A~3C, and the implanting apparatus 200 clamping the intervertebral cage 100 is inserted into the hollowed catheter 300. Meanwhile, the terminal end of the sleeve 210 contacts each connecting portion 120, and the two ends of the coupling column 222 respectively press against the two first inner arc surfaces 120p1. Here, a force applying direction Df is, for example, a direction from the circle center N21 of the first inner arc surface 120p1 to the circle center N11 of the fillet 119 as illustrated in FIG. 1A. When the surgeon percusses the terminal end of the implanting apparatus 200 along the force applying direction Df, since the intervertebral cage 100 moves along the force applying direction Df, that is, moves straightforward on the line segment w3 (the line segment connecting the circle center N21 of the first inner arc surface 120p1 to the circle center N11 of the fillet 119 as illustrated in FIG. 1A), the intervertebral cage 100 can be smoothly percussed into the intervertebral disc Bd. Therefore, the intervertebral cage 100 will not be deviated to damage the nerve or the surrounding tissues during the implantation.

Figure 4D:
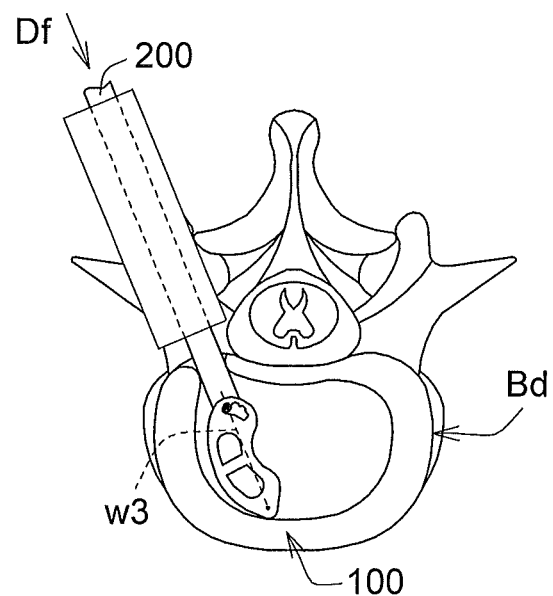

As indicated in FIG. 4D, when the intervertebral cage 100 is percussed into the intervertebral disc Bd, the surgeon will keep percussing the intervertebral cage 100 along the force applying direction Df, and at the same time identify the positions of the positioning members 150 (as shown in FIGS. 1A, 1E and 1F) with a surgical C-arm. Therefore, the position of the intervertebral cage 100 inside the intervertebral disc Bd is obtained. When the intervertebral cage 100 contacts the front of the intervertebral disc Bd to be obstructed by resistance, and the location of the intervertebral cage 100 is identified with the C-arm, the surgeon will stop percussing the intervertebral cage 100.

Figure 4E:
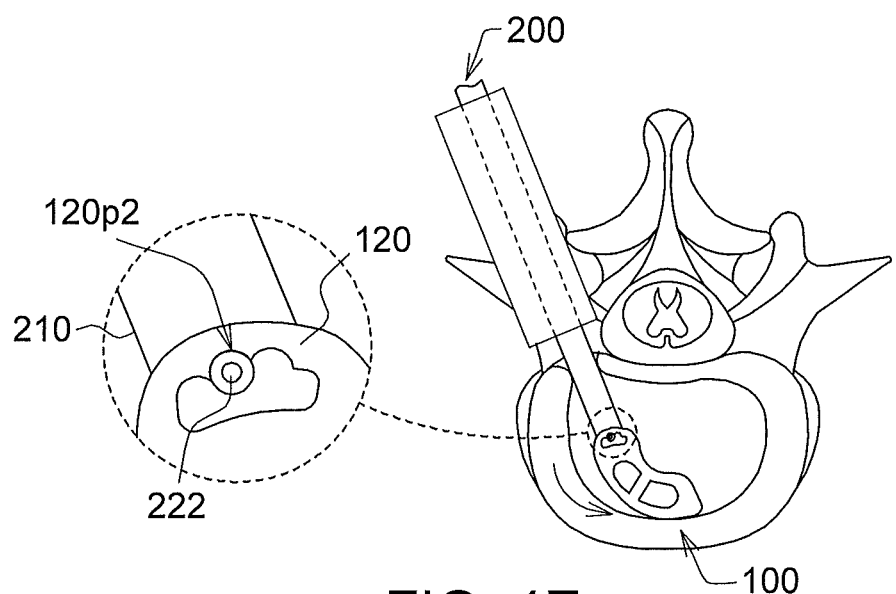

As indicated in FIG. 4E, the positions at which the sleeve 210 and the coupling column 222 of the implanting apparatus 200 clamp the connecting portions 120 of the intervertebral cage 100 are changed, so that the terminal end of the sleeve 210 contacts each connecting portion 120, and the two ends of the coupling column 222 respectively press against the two second inner arc surfaces 120p2. Then, as the surgeon percusses the terminal end of the implanting apparatus 200, the intervertebral cage 100 clamped by the implanting apparatus 200 is rotated around the circle center of the coupling column 222 with respect to the implanting apparatus 200. Meanwhile, when the surgeon percusses the terminal end of the implanting apparatus 200 to move the intervertebral cage 100 towards the front of the intervertebral disc Bd but is obstructed by resistance, the surgeon will stop percussing as soon as the location of the intervertebral cage 100 is identified with the C-arm.

Figure 4F:
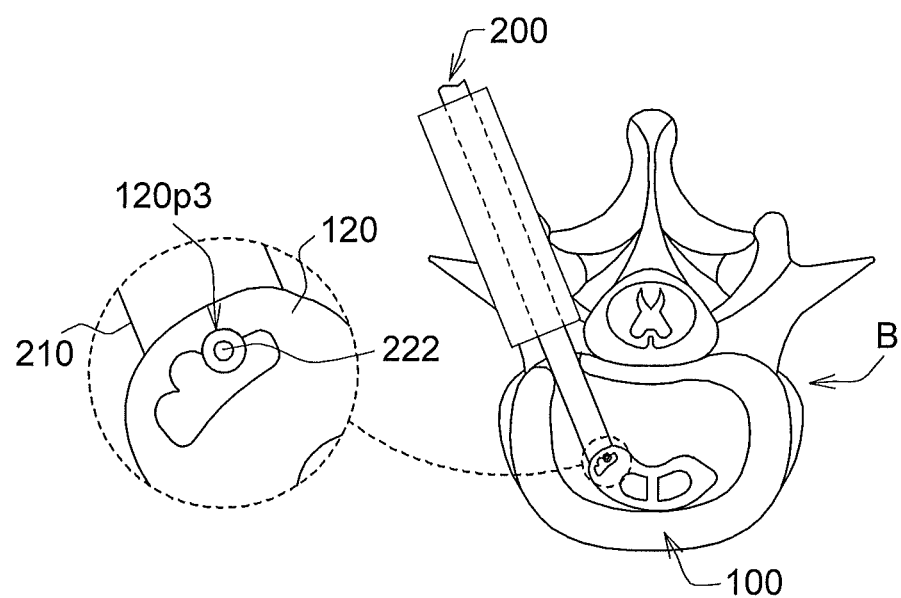

As indicated in FIG. 4F, the positions at which the sleeve 210 and the coupling column 222 of the implanting apparatus 200 clamp the connecting portions 120 of the intervertebral cage 100 are changed again, so that the terminal end of the sleeve 210 contacts each connecting portion 120, and the two ends of the coupling column 222 respectively press against two third inner arc surfaces 120p3. Then, when the surgeon percusses the terminal end of the implanting apparatus 200, the intervertebral cage 100 clamped by the implanting apparatus 200 is rotated around the circle center of the coupling column 222 with respect to the implanting apparatus 200. Thus, the intervertebral cage 100 will be eventually located at the front of the vertebral body B, that is, the main force receiving region of the vertebral body B. Since the outline of the intervertebral cage 100 of the present embodiment of the disclosure is close to that of the vertebral body B, and the final position of the intervertebral cage 100 after the implantation is within the main force receiving region of the vertebral body B, the intervertebral cage 100 can provide support under the circumstances that the received force is uniform.

Through the cooperation between the first inner arc surfaces 120p1, the second inner arc surfaces 120p2 and the third inner arc surfaces 120p3 of the intervertebral cage 100 and the coupling column 222 of the implanting apparatus 200, the intervertebral cage 100 of the present embodiment of the disclosure can be rotated for 45~75 degrees to make the wound created during the implantation process illustrated in FIGS. 4A~4F smaller than 3 cm. Thus, the risk of massive blood loss caused by a large wound can be avoided, and the surrounding tissues of the spine will not be damaged easily. In addition, the required recovery time can be reduced, and the sequelae such as lower back pain or weakness can be avoided.

According to the intervertebral cage, the implanting apparatus and the operating method thereof disclosed in the above embodiments of the disclosure, the coupling column and the sleeve of the implanting apparatus clamp the intervertebral cage at different positions for implanting the intervertebral cage, so that the wound which is smaller than 3 cm is created during the implantation process. Moreover, the cooperation of the lateral convex surface and the inclined surface makes the implantation easier.

While the disclosure has been described by way of example and in terms of the exemplary embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An intervertebral cage used for being implanted into a location between two adjacent vertebral bodies, wherein the intervertebral cage comprises:
    a body having a lateral convex surface, a lateral concave surface, an inclined surface, a connecting surface and a fillet located between the inclined surface and the lateral convex surface, wherein the lateral convex surface, the inclined surface, the lateral concave surface and the connecting surface are connected sequentially; and
    at least one connecting portion comprising a main portion and a first protrusion, wherein the main portion is connected to the connecting surface of the body and has at least one through hole, the first protrusion is protruded from the main portion into the through hole in a direction towards the connecting surface so as to form a first inner arc surface and a second inner arc surface and a first angle contained between the inclined surface and a line segment connecting the circle center of the fillet to the circle center of the first inner arc surface ranges 0~89 degrees;
    wherein the maximum width of the intervertebral cage is a distance between a first line and a second line, the first line is substantially parallel to a tangent line of the lateral convex surface, the second line is substantially parallel to the first line, and the distance between the inclined surface and the first line decreases gradually along a direction away from the connecting portion.

2. The intervertebral cage according to claim 1, wherein the first angle contained between the inclined surface and the line segment connecting the circle center of the fillet to the circle center of the first inner arc surface ranges 0~60 degrees.

3. The intervertebral cage according to claim 1, wherein the first angle contained between the inclined surface and the line segment connecting the circle center of the fillet to the circle center of the first inner arc surface ranges 0~45 degrees.

4. The intervertebral cage according to claim 1, wherein the body further has a top surface and a bottom surface opposite to the top surface, the top surface and the bottom surface are both located between the lateral convex surface and the lateral concave surface, and a second angle contained between the top surface and the bottom surface at the junction between the inclined surface and the lateral convex surface ranges 1~79 degrees.

5. The intervertebral cage according to claim 4, wherein the second angle contained between the top surface and the bottom surface at the junction between the inclined surface and the lateral convex surface ranges 1~35 degrees.

6. The intervertebral cage according to claim 4, wherein the second angle contained between the top surface and the bottom surface at the junction between the inclined surface and the lateral convex surface ranges 1~90 degrees.

7. The intervertebral cage according to claim 1, wherein the connecting portion further comprises a second protrusion protruded from the main portion into the through hole in a direction towards the connecting surface so as to form a third inner arc surface, and the second inner arc surface is located between the third inner arc surface and the first inner arc surface.

8. The intervertebral cage according to claim 7, wherein the circle center of the first inner arc surface, the circle center of the second inner arc surface and the circle center of the third inner arc surface are three points on a circle, a first line segment connects the circle center of the circle to the circle center of the first inner arc surface, a second line segment connects the circle center of the circle to the circle center of the third inner arc surface, and a third angle contained between the first line segment and the second line segment ranges 0~179 degrees.

9. The intervertebral cage according to claim 8, wherein the third angle contained between the first line segment and the second line segment ranges 0~90 degrees.

10. The intervertebral cage according to claim 8, wherein the third angle contained between the first line segment and the second line segment ranges 45~75 degrees.

11. The intervertebral cage according to claim 7, wherein a terminal end of a sleeve and a coupling column of an implanting apparatus are used for clamping the connecting portion, so that the connecting portion is located between the terminal end of the sleeve and the coupling column, the terminal end of the sleeve contacts the connecting portion, and one end of the coupling column presses against the first inner arc surface, the second inner arc surface or the third inner arc surface.

12. The intervertebral cage according to claim 11, wherein the outline of an outer surface of the terminal end of the sleeve is substantially identical to that of an outer surface of the connecting portion.

13. The intervertebral cage according to claim 11, wherein the outline of an outer surface of the end of the coupling column is substantially identical to that of the first inner arc surface, the second inner arc surface and the third inner arc surface.

14. The intervertebral cage according to claim 1, wherein the connecting portion and the body are integrally formed in one piece.

15. The intervertebral cage according to claim 1, wherein the intervertebral cage is made from an absorbable polymer material, a non-absorbable polymer material, a metal, a ceramic material, a bone material or a combination thereof.

16. The intervertebral cage according to claim 1, further comprising:
    a positioning member disposed in the body.

* * * * *